United States Patent
Jeong et al.

(10) Patent No.: US 11,794,162 B2
(45) Date of Patent: Oct. 24, 2023

(54) HEAT EXCHANGE SYSTEM AND PREPARATION SYSTEM OF DIESTER-BASED COMPOSITION COMPRISING THE SAME

(71) Applicant: LG CHEM, LTD., Seoul (KR)

(72) Inventors: Jae Hun Jeong, Daejeon (KR); Sung Kyu Lee, Daejeon (KR); Yeon Uk Choo, Daejeon (KR); Hyoung Jun, Daejeon (KR); Chan Hyu Jin, Daejeon (KR)

(73) Assignee: LG Chem, Ltd., Seoul (KR)

( * ) Notice: Subject to any disclaimer, the term of this patent is extended or adjusted under 35 U.S.C. 154(b) by 64 days.

(21) Appl. No.: 17/600,284

(22) PCT Filed: Jul. 2, 2020

(86) PCT No.: PCT/KR2020/008682
§ 371 (c)(1),
(2) Date: Sep. 30, 2021

(87) PCT Pub. No.: WO2021/002707
PCT Pub. Date: Jan. 7, 2021

(65) Prior Publication Data
US 2022/0203323 A1    Jun. 30, 2022

(30) Foreign Application Priority Data

Jul. 4, 2019 (KR) .................. 10-2019-0080463

(51) Int. Cl.
*B01J 19/00* (2006.01)
*B01D 3/14* (2006.01)
*B01J 19/24* (2006.01)

(52) U.S. Cl.
CPC .......... *B01J 19/0013* (2013.01); *B01D 3/143* (2013.01); *B01J 19/245* (2013.01); *B01J 2219/00074* (2013.01)

(58) Field of Classification Search
CPC . B01D 3/00; B01D 3/009; B01D 3/06; B01D 3/14; B01D 3/143; B01J 19/00;
(Continued)

(56) References Cited

U.S. PATENT DOCUMENTS

| 4,467,109 A | 8/1984 | Tahara et al. |
| 4,956,493 A | 9/1990 | Ueoka et al. |

(Continued)

FOREIGN PATENT DOCUMENTS

| EP | 0 289 178 A1 | 11/1988 |
| EP | 2851393 A1 | 3/2015 |

(Continued)

OTHER PUBLICATIONS

Rahman, et al. (2004). The Plasticizer Market: An Assessment Of Traditional Plasticizers And Research Trends To Meet New Challenges. Prog. Polym. Sci. vol. 29. pp. 1223-1248.
(Continued)

*Primary Examiner* — Natasha E Young
(74) *Attorney, Agent, or Firm* — Bryan Cave Leighton Paisner LLP

(57) ABSTRACT

The present disclosure relates to a heat exchange system which is capable of saving energy consumed in a whole process by exchanging heat of different streams from each other, included in a continuous preparation system of a diester-based composition.

13 Claims, 6 Drawing Sheets

(58) Field of Classification Search
CPC .... B01J 19/0006; B01J 19/0013; B01J 19/24; B01J 19/245; B01J 2219/00; B01J 2219/00049; B01J 2219/00051; B01J 2219/00074; B01J 2219/00274; B01J 2219/00277; B01J 2219/00495
See application file for complete search history.

(56) References Cited

U.S. PATENT DOCUMENTS

| | | | |
|---|---|---|---|
| 5,659,072 | A | 8/1997 | Bessalem et al. |
| 8,624,073 | B1 | 1/2014 | Yang et al. |
| 9,127,141 | B2 * | 9/2015 | Lee .................. C08K 5/12 |
| 2002/0035282 | A1 | 3/2002 | Suppes |
| 2003/0149289 | A1 | 8/2003 | Suppes |
| 2009/0264671 | A1 | 10/2009 | Noh et al. |
| 2017/0297998 | A1 * | 10/2017 | Schraut .............. B01J 19/0066 |
| 2018/0135914 | A1 | 5/2018 | Kim et al. |
| 2019/0241715 | A1 | 8/2019 | Kim et al. |
| 2019/0263745 | A1 | 8/2019 | Lee et al. |
| 2021/0040026 | A1 | 2/2021 | Lee et al. |

FOREIGN PATENT DOCUMENTS

| | | |
|---|---|---|
| JP | S48-030046 A | 4/1973 |
| JP | S57-42656 A | 3/1982 |
| JP | 2019-529605 A | 10/2019 |
| KR | 10-0174642 B1 | 11/1998 |
| KR | 10-0806353 B1 | 2/2008 |
| KR | 10-2012-0022020 A | 3/2012 |
| KR | 10-2013-0042743 A | 4/2013 |
| KR | 10-1663586 B1 | 10/2016 |
| KR | 10-2016-0150150 A | 12/2016 |
| KR | 10-2018-0131026 A | 12/2018 |
| KR | 10-2019-0027622 A | 3/2019 |
| KR | 10-2019-0027623 A | 3/2019 |
| WO | 2019-050281 A1 | 3/2019 |

OTHER PUBLICATIONS

Janjua, et al. (2007). Systemic Uptake of Diethyl Phthalate, Dibutyl Phthalate, and Butyl Paraben Following Whole-Body Topical Application and Reproductive and Thyroid Hormone Levels in Humans. Environ. Sci. Technol. vol. 41. pp. 5564-5570.

* cited by examiner

[FIG. 1]
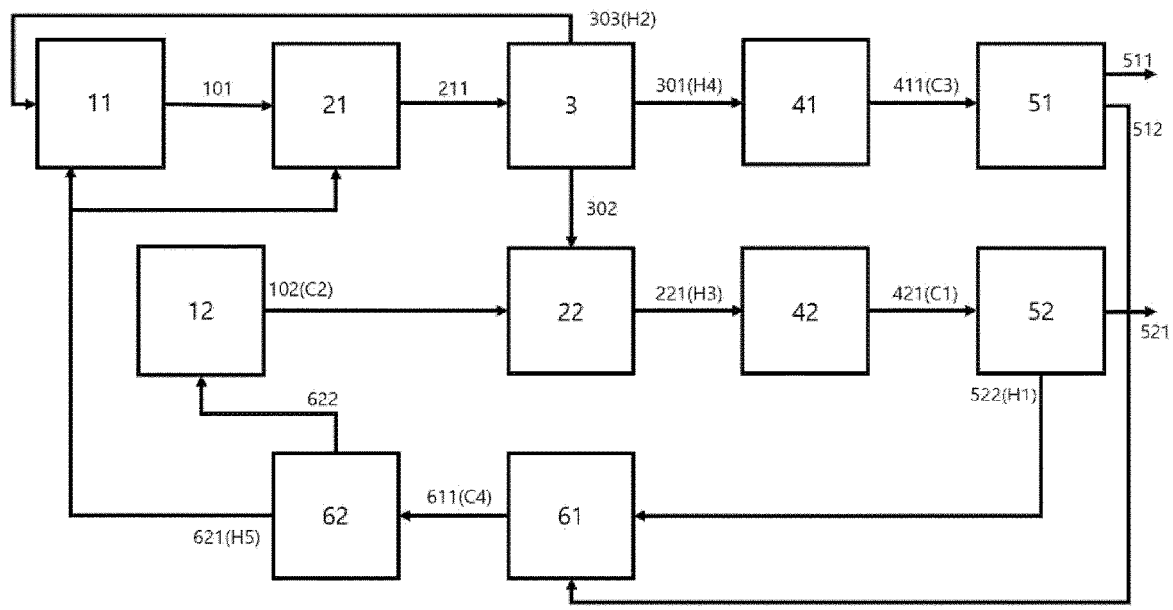
[FIG. 2]
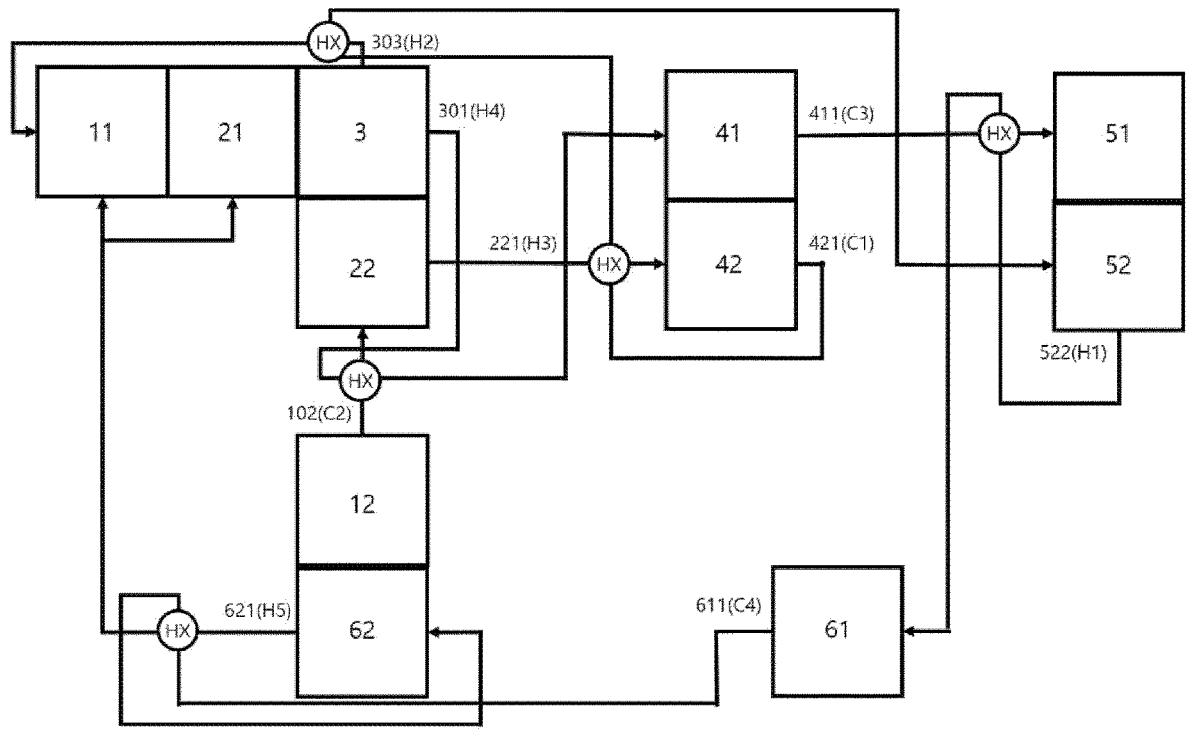

[FIG. 3]
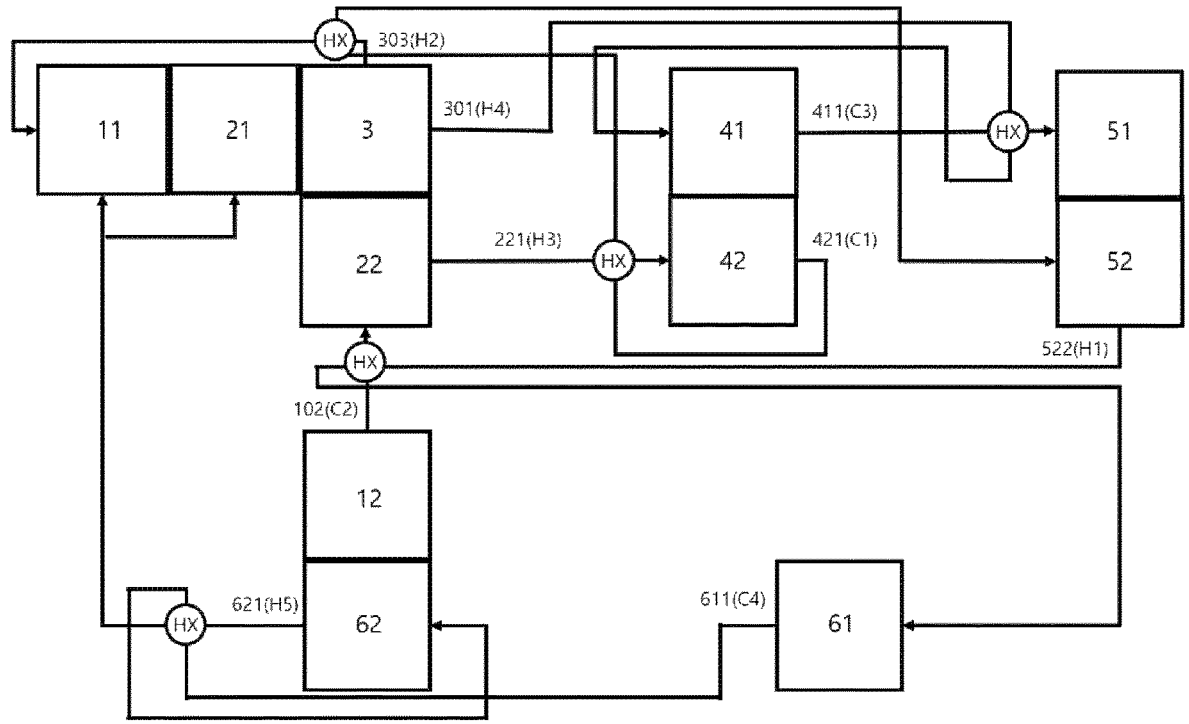
[FIG. 4]
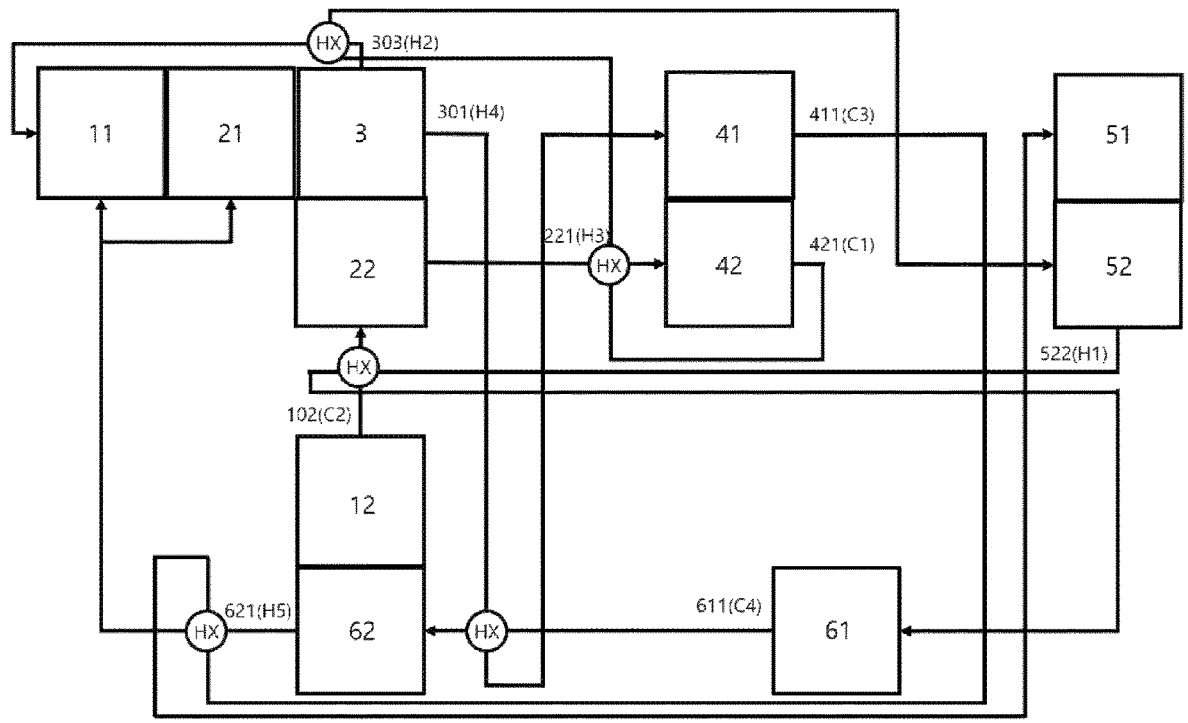

[FIG. 5]
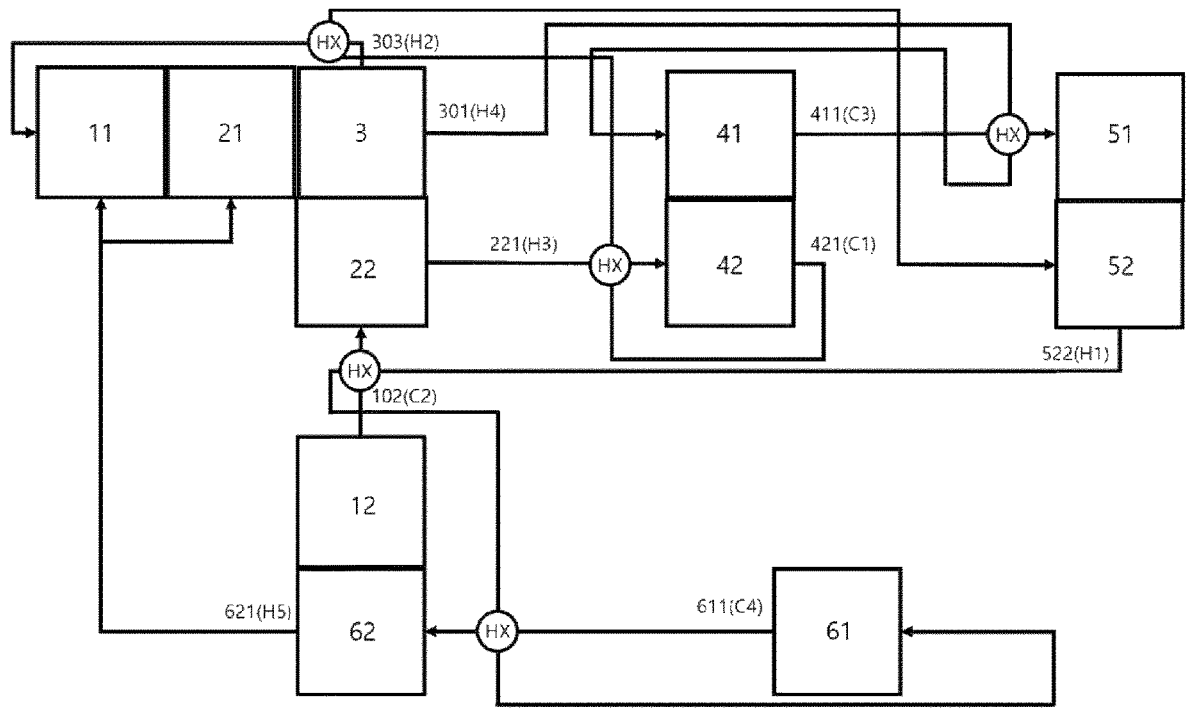
[FIG. 6]
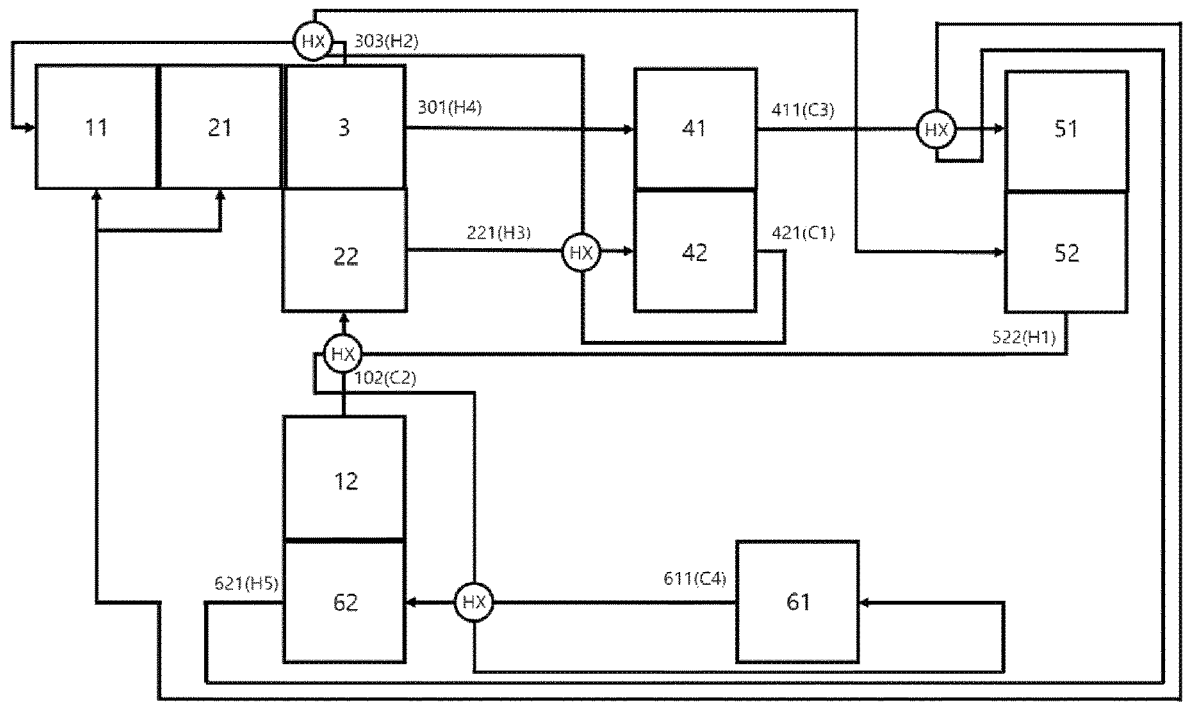

[FIG. 7]
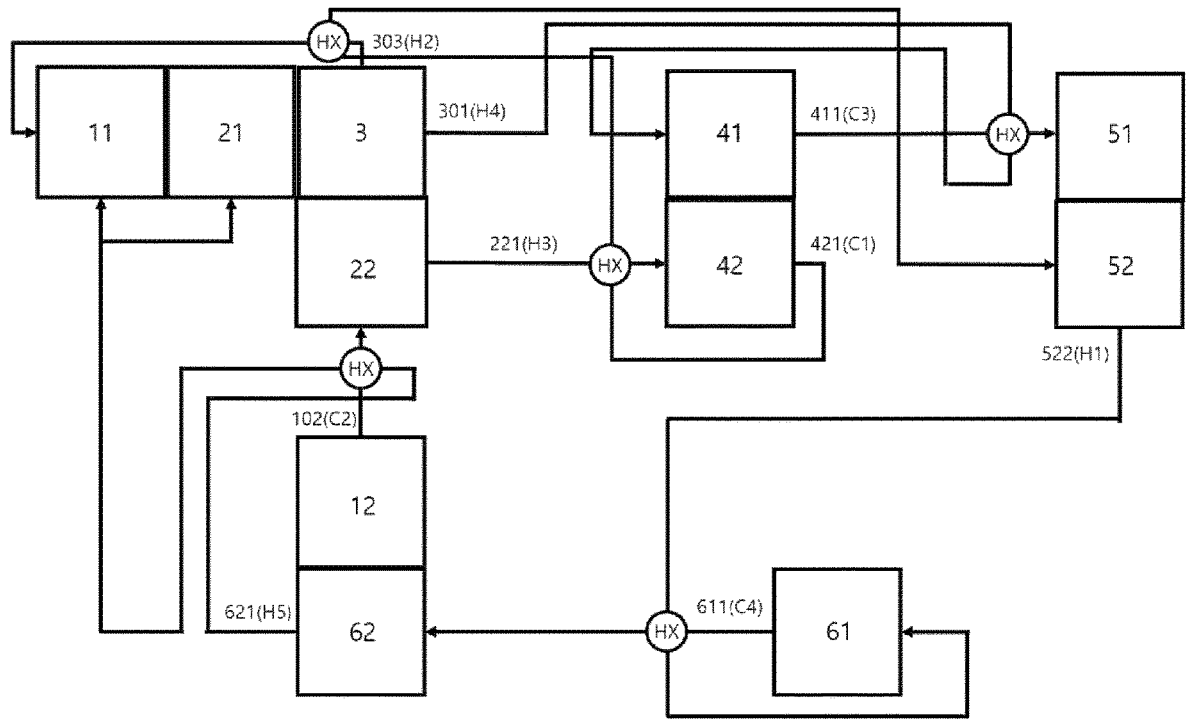
[FIG. 8]
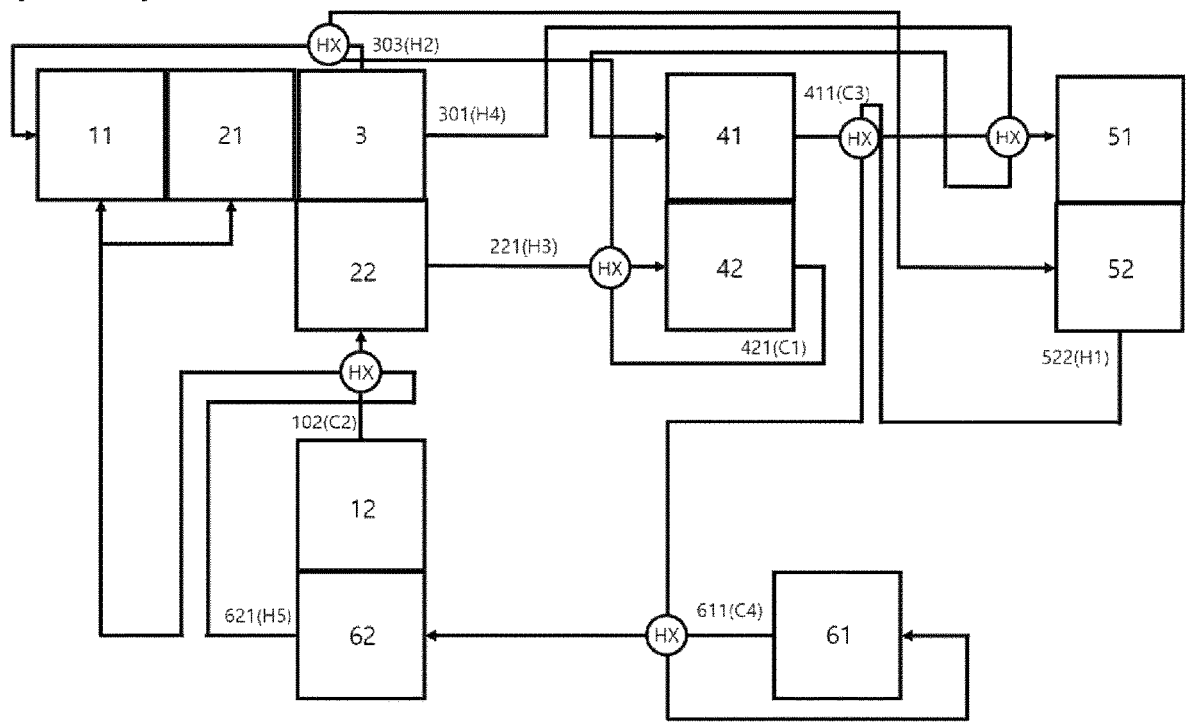

[FIG. 9]
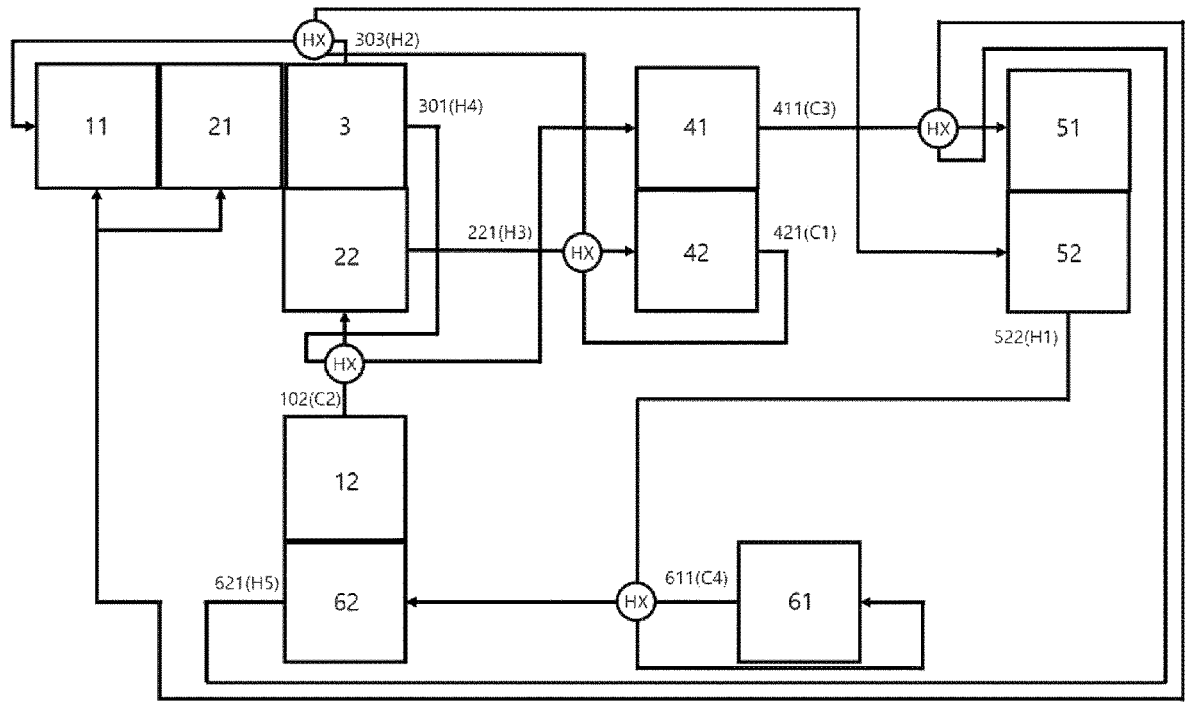
[FIG. 10]
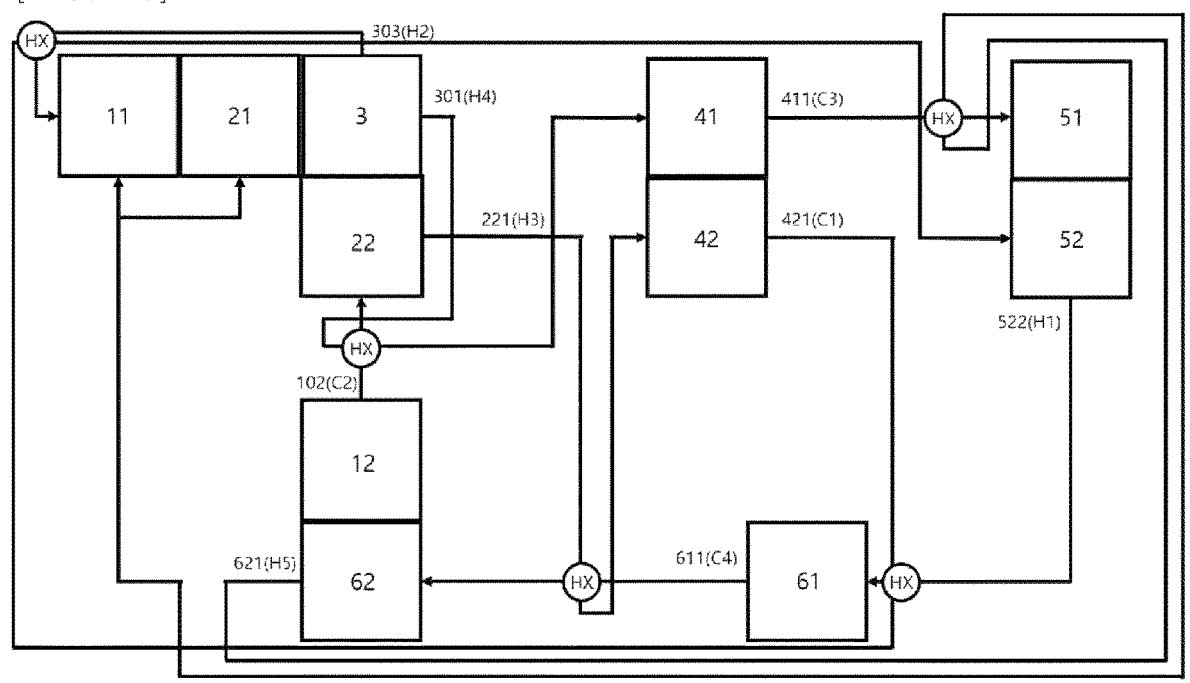

[FIG. 11]
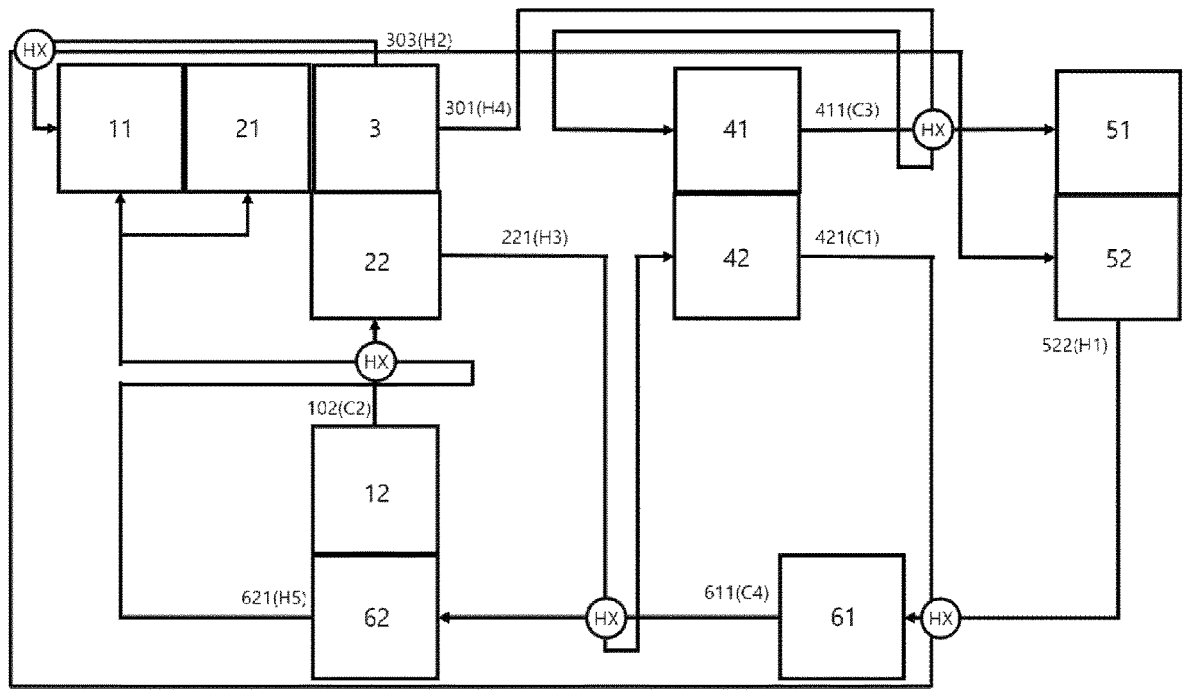

HEAT EXCHANGE SYSTEM AND PREPARATION SYSTEM OF DIESTER-BASED COMPOSITION COMPRISING THE SAME

TECHNICAL FIELD

Cross-Reference to Related Applications

The present application is a National Phase entry pursuant to 35 U.S.C. § 371 of International Application No. PCT/KR2020/008682, now WO 2021/002707, filed on Jul. 2, 2020, and claims the benefit of and priority to Korean Patent Application No. 10-2019-0080463, filed on Jul. 4, 2019, in the Korean Intellectual Property Office, all of which are hereby incorporated by reference in their entirety for all purposes as if fully set forth herein.

TECHNICAL FIELD

The present invention relates to a heat exchange system which is designed for allowing efficient heat exchange and a preparation system of a diester-based composition comprising the heat exchange system.

BACKGROUND ART

Phthalate-based plasticizers account for 92% of the world plasticizer market until the 20th century (see Mustafizur Rahman and Christopher S. Brazel "The plasticizer market: an assessment of traditional plasticizers and research trends to meet new challenges" Progress in Polymer Science 2004, 29, 1223-1248) and are added as additives for mostly imparting polyvinyl chloride (hereinafter, will referred to as PVC) with flexibility, durability, cold resistance, etc., and reducing the viscosity during melting to improve processability to PVC in various contents and widely used for intimate relation in real life and inevitable direct contact with the human body from hard products such as hard pipes to soft products which may be used in food package materials and blood bags, flooring materials, etc., because of the softness and well-stretching properties thereof when compared to any other materials.

However, despite the compatibility with PVC and excellent softness imparting properties of the phthalate-based plasticizers, recently, in case of using the PVC products containing the phthalate-based plasticizers in real life, controversy over harmfulness has been suggested in that the phthalate-based plasticizers might be released little by little out of the products and act as suspected endocrine disruptors (environmental hormone) and a carcinogen with a heavy metal level (see N. R. Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2007, 41, 5564-5570). Particularly, after a report has been announced in 1960s in America that the most used di-(2-ethylhexyl) phthalate (DEHP) among phthalate-based plasticizers is released out of PVC products, with added interest on environmental hormone in 1990s, various studies on the harmfulness of phthalate plasticizers to the human body and worldwide environmental regulations have been started.

Accordingly, in order to cope with environmental hormone issues and environmental regulations due to the release of phthalate-based plasticizers, particularly, di(2-ethylhexyl) phthalate, many researchers have proceeded research on developing a novel non-phthalate-based replaceable plasticizers excluding anhydrous phthalic acid which has been used for preparing di(2-ethylhexyl) phthalate, developing phthalate-based plasticizers which may replace di(2-ethylhexyl) phthalate, which may, though phthalate-based, suppress the release of the plasticizer and be used industrially, and developing release-suppressing technique by which the release of phthalate-based plasticizers may be suppressed to markedly reduce the harmfulness to the human body and which may coincide with environmental standards.

As described above, the development of materials which are free from environmental issues and replaceable with di(2-ethylhexyl) phthalate which is a diester-based plasticizer and has the existing environmental issues, is actively being conducted, research on developing diester-based plasticizers having excellent physical properties and research on equipment for preparing such plasticizers are actively being conducted, and the design for more efficient, economic and simple processes in view of process design is required.

Meanwhile, in a process for preparing the diester-based plasticizer above, a batch type process is applied in most industrial sites, and an invention on a gas-liquid separation system for refluxing unreacted materials in a reactor and effective removal of by-products in a batch type process (Korean Patent Publication No. 10-2019-0027622), an invention on a system in which equipment for first direct esterification reaction and equipment for second trans esterification are combined for the simplification of equipment for a batch type process (Korean Patent Publication No. 10-2019-0027623), etc. have been disclosed. However, such inventions employ a batch type process, and there are limitations on the improvement of refluxing amount or steam amount, productivity is very low, and there are limitations on technique applicable for improvement.

In addition, as a continuous process, an invention relating to a process composing a reaction part through connecting two or more reactors in series (Korean Registered Patent Publication No. 10-1663586) has been disclosed, but only with the control of the reaction temperature of continuously connected reactors, the improvement of overall processability is limited.

PRIOR ART DOCUMENTS

Patent Documents (Patent Document 1) Korean Patent Publication No. 10-2019-0027622
(Patent Document 2) Korean Patent Publication No. 10-2019-0027623
(Patent Document 3) Korean Registered Patent Publication No. 10-1663586

Non-Patent Documents (Non-patent document 1) Mustafizur Rahman and Christopher S. Brazel "The plasticizer market: an assessment of traditional plasticizers and research trends to meet new challenges" Progress in Polymer Science 2004, 29, 1223-1248
(Non-patent document 2) N. R. Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2007, 41, 5564-5570

DISCLOSURE OF THE INVENTION

Technical Problem

The present invention provides a heat exchange system which may be applied to a continuously operated preparation system of a diester-based composition and may save steam and a cooling agent used in a whole process by optimizing heat exchange between streams having different temperatures, and a preparation system of a diester-based composition comprising the heat exchange system.

Technical Solution

The present invention provides, in a preparation system of a diester-based composition, a heat exchange system comprising a heat exchange part composed for heat exchange between one or more high temperature streams selected from the group consisting of a first high temperature stream discharged from a second purification part and injected into a mixed alcohol tank, a second high temperature stream discharged from a preliminary purification part and injected into a first alcohol tank, a third high temperature stream discharged from a trans reaction part and injected into a second washing part, a fourth high temperature stream discharged from the preliminary purification part and injected into a first washing part, and a fifth high temperature stream discharged from a separation part and injected into at least one of the first alcohol tank and a reaction part, and one or more low temperature streams selected from the group consisting of a first low temperature stream discharged from the second washing part and injected into the second purification part, a second low temperature stream discharged from a second alcohol tank and injected into the trans reaction part, a third low temperature stream discharged from the first washing part and injected into a first purification part, and a fourth low temperature stream discharged from the mixed alcohol tank and injected into the separation part.

Advantageous Effects

In the heat exchange system of the present invention, by pairing up multiple high temperature streams having relatively higher temperature and multiple low temperature streams having relatively lower temperature and allowing heat exchange, the amounts used of steam and a cooling agent in a whole process may be minimized.

BRIEF DESCRIPTION OF THE DRAWINGS

FIG. 1 illustrates the conventional continuous operating preparation system of a diester-based composition, to which the heat exchange system of the present invention is applicable.

FIGS. 2 to 11 illustrate preparation systems of a diester-based composition, to which the heat exchange systems according to Examples 1 to 10 of the present invention are applied, respectively.

BEST MODE FOR CARRYING OUT THE INVENTION

Hereinafter, preferred embodiments will be suggested to assist the understanding of the present invention. However, the embodiments are only for illustrating the present invention and do not limit the scope of the present invention.

Examples 1 to 10

Heat exchange systems were composed as shown in FIGS. 2 to 11 and regarded as Examples 1 to 10, respectively, and a case of a process for the same diester-based preparation without a heat exchange system was regarded as Comparative Example. The amounts used of total energy, the amounts used of cooling water, the amounts used of steam and heat exchange ratios in Examples 1 to 10 were calculated based on the Comparative Example through a process simulation program, and are shown in Table 1 below. The heat exchange ratio was calculated by dividing heat exchange calories by the amount used of total energy.

TABLE 1

|  | Amount used of energy (%) | Amount used of cooling water (%) | Amount used of steam (%) | Heat exchange ratio (%) |
|---|---|---|---|---|
| Comparative Example | 100 | 100 | 100 | 0 |
| Example 1 | 72 | 53 | 33 | 38 |
| Example 2 | 74 | 56 | 38 | 34 |
| Example 3 | 75 | 57 | 40 | 33 |
| Example 4 | 74 | 56 | 38 | 34 |
| Example 5 | 75 | 57 | 40 | 33 |
| Example 6 | 74 | 56 | 38 | 34 |
| Example 7 | 73 | 55 | 36 | 36 |
| Example 8 | 75 | 57 | 40 | 33 |
| Example 9 | 80 | 66 | 51 | 25 |
| Example 10 | 79 | 65 | 50 | 26 |

It was confirmed that all Examples 1 to 10 saved energy by at least 20% when compared to Comparative Example, the amount used of cooling water was saved to maximum half, and the amount used of steam was saved to maximum ⅓. Accordingly, it was confirmed that the heat exchange system of the present invention can provide excellent energy efficiency.

MODE FOR CARRYING OUT THE INVENTION

Hereinafter, the present invention will be explained in more detail.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

In the present invention, "high temperature stream" refers to a stream having a relatively high temperature than other streams, particularly, a stream having a temperature of 150 to 250° C.

In the present invention, "low temperature stream" refers to a stream having a relatively low temperature than other streams, particularly, a stream having a temperature of 20 to 130° C.

In the present invention, "dicarboxylic acid" commonly refers to a compound having two carboxylic acid groups, particularly, one or more compounds selected from the group consisting of phthalic acid, terephthalic acid, isophthalic acid and cyclohexane dicarboxylic acid.

In the present invention, "first alcohol" and "second alcohol" refer to primary alcohols with 3 to 12 carbon atoms and include both linear type and branched type, and the first alcohol and the second alcohol are different alcohols from each other.

The heat exchange system of the present invention allows effective heat exchange between streams transported in a continuously operated preparation system of a diester-based composition. Accordingly, the continuously operated preparation system of a diester-based composition will be explained first, and then, the heat exchange system will be explained.

Preparation System of Diester-Based Composition

The basic preparation system of a diester-based composition, which is applicable to the heat exchange system of the present invention will be explained below. The following is for explaining an embodiment of the preparation system of a diester-based composition, applicable to the heat exchange system of the present invention, and it is obvious to apply the heat exchange system provided in the present invention even though some elements of the system are removed, added or modified within a range maintaining the basic structure of the preparation system of a diester-based composition explained below.

An embodiment of the preparation system of a diester-based composition is shown in FIG. 1, and the preparation system of a diester-based composition will be explained referring to FIG. 1.

The preparation system of a diester-based composition includes a first alcohol tank (11), a second alcohol tank (12), a reaction part (21), a trans reaction part (22), a preliminary purification part (3), a first washing part (41), a second washing part (42), a first purification part (51), a second purification part (52), a mixed alcohol tank (61) and a separation part (62).

The first alcohol tank and the second alcohol tank contain a first alcohol and a second alcohol, corresponding to reaction raw materials. The first alcohol is used for the esterification reaction with carboxylic acid, and the second alcohol is used for the trans esterification reaction with an ester compound, a first alcohol stream (101) is transported to the reaction part, and a second alcohol stream (102) is transported to the trans reaction part for the esterification reaction and the trans esterification reaction afterward. The shape of the first alcohol tank and the second alcohol tank is not specifically limited, and any shape can be used as long as the first alcohol and the second alcohol can be stored without modification and can be easily transported.

In the reaction part (21), the esterification reaction of the first alcohol and the dicarboxylic acid is performed. Though the injection stream of the dicarboxylic acid is not shown in FIG. 1, the dicarboxylic acid can be directly injected into the reaction part, or can be mixed and injected into the first alcohol stream prior to the injection into the reaction part. The reaction part can be provided with an internal space for the esterification reaction, and can be provided with a catalyst injection part for injecting a catalyst required for the reaction or a heating means for applying heat required for the esterification reaction. Common reaction parts used for the esterification reaction can be used without specific limitation.

Meanwhile, since the temperature at which the esterification reaction is mostly performed is a higher temperature than the boiling point of water which is the by-product of the esterification reaction with an alcohol reaction raw material, the vaporization of water and alcohol is generated during the esterification reaction, and a sufficient conversion rate cannot be accomplished. In order to prevent this defect, an excessive amount of alcohol is generally injected than the alcohol equivalent required in practice. Accordingly, unreacted alcohol is included in the reaction product in addition to an ester compound after finishing the reaction, and the first reaction product produced by the esterification reaction in the reaction part also includes an ester compound and unreacted first alcohol. The first reaction stream (211) is transported to the preliminary purification part (3) to remove the unreacted alcohol included in the reaction product.

In the preliminary purification part (3) to which the first reaction product is injected, the unreacted alcohol in the reaction product, i.e., the unreacted first alcohol is removed. The "removal" can be performed through known methods such as distillation, and any methods used for separating an ester compound and an alcohol compound can be applied without specific limitation. For example, the preliminary purification part can have a shape of a column, a distillation column, etc. The unreacted first alcohol stream (303) removed from the preliminary purification part is transported to the first alcohol tank (11) to be used again as the reaction raw material. Meanwhile, the first reaction product (hereinafter, will be referred to as "purified product") from which the unreacted first alcohol is removed, is divided into different parts and injected to obtain two types of products. One part (301) is transported to the first washing part to obtain a first diester-based composition, and the remainder (302) is transported to the trans reaction part to obtain a second diester-based composition.

The purified product (302) transported to the trans reaction part undergoes trans esterification reaction with the second alcohol (102) injected from the second alcohol tank to produce a second reaction product. The trans reaction part can also be provided with an interior space, a catalyst injection part or a heating means as in the above-described reaction part, and any one known to be used for trans esterification reaction can be used without specific limitation.

Meanwhile, the second reaction product can include the second alcohol in the reaction product, corresponding to a reaction raw material like the first reaction product, and can include the first alcohol produced through trans esterification reaction or un-removed in advance, considering the first alcohol is produced instead of water by trans esterification. The second reaction product stream (221) is transported to the second washing part to obtain a second diester-based composition afterward.

Both the first reaction product (301) transported to the first washing part and the second reaction product (221) transported to the second washing part become the targets of neutralization and washing. Since an acidic catalyst is generally used for esterification reaction and trans esterification reaction, the neutralization and washing of the remaining catalyst is performed in the first washing part and the second washing part. After performing the neutralization and washing, the temperature of the first reaction product (hereinafter, will be referred to as "first neutralized product") and the second reaction product (hereinafter, will be referred to as "second neutralized product") streams is lowered due to a washing step, and the streams are transported to the first purification part and the second purification part to remove the first alcohol or a mixed alcohol, which can remain.

In the first purification part, the first alcohol in the transporting first neutralized product stream (411) is removed, and a first diester-based composition (511) corresponding to a final product is obtained. In addition, in the second purification part, the mixed alcohol in the transporting second neutralized product stream (421) is removed, and a second diester-based composition (521) corresponding to a final product is obtained. The removal of the alcohol in the first purification part and the second purification part can be performed through well-known methods such as distillation in the previous preliminary purification part, and any methods used for separating an ester compound and an alcohol compound can be applied without specific limitation. For example, the first purification part and the second purification part can have a shape of a flash drum, a column, a distillation column, etc.

Meanwhile, the first alcohol (512) removed in the first purification part and the mixed alcohol (522) removed in the second purification part are transported to the mixed alcohol tank (61). The mixed alcohol tank (61) is for temporarily storing the mixed alcohol of the first alcohol and the second alcohol, and the shape or position thereof are not specifically limited as long as the modification of an alcohol is not induced like the first alcohol tank and the second alcohol tank. The mixed alcohol stream (611) of the mixed alcohol tank is then injected into a separation part (62) and separated into a first alcohol stream (621) and a second alcohol stream (622), and then, the first alcohol stream is transported to at least one of the first alcohol tank and the reaction part, and the second alcohol stream is transported to the second alcohol tank.

The separation part is for separating the mixed alcohol and can preferably have a shape such as a distillation column capable of separating a mixture using a boiling point difference, because the first alcohol and the second alcohol have a boiling point difference.

The preparation system of a diester-based composition is continuously operated and is particularly suitable to apply a heat exchange system, because the flow rate of each stream is maintained constant. If the preparation system is discontinuously operated, the application of the heat exchange system of the present invention is not easy.

Heat Exchange System

The present invention provides a heat exchange system which can be applied to the above-explained preparation system of a diester-based composition. In the continuous preparation process of a diester-based composition, multiple high temperature streams having relatively high temperature and multiple low temperature streams having relatively low temperature are present. In addition, a portion of the high temperature streams and a portion of the low temperature streams can require cooling or heating prior to undergoing a subsequent process.

For example, a purified stream through a method such as distillation can have a relatively high temperature by heating during a distillation process, and the purified stream is required to be cooled prior to undergoing a subsequent process, because some vaporized components are required to be liquefied by reducing the temperature to store the purified stream in an apparatus such as a tank. In addition, a stream inflowing into a washing part for washing which is carried out at a relatively low temperature is required to be cooled, and a stream discharged from the washing part can have a relatively low temperature, and since the stream is required to be heated through a process such as distillation in a purification step after washing, and accordingly, if the stream is partially heated prior to injecting to a purification step, energy consumed in the purification step can be reduced.

As described above, in the continuous preparation system of a diester-based composition, multiple high temperature streams and low temperature streams, requiring cooling or heating are present, and the inventors of the present invention found that energy consumed for cooling and heating each stream in a subsequent step could be saved by designing a heat exchange part for exchanging heat between the high temperature streams and the low temperature streams, and completed the present invention.

Particularly, the heat exchange system of the present invention in the above-explained preparation system of a diester-based composition can include a heat exchange part composed for heat exchanging from each other, one or more high temperature streams selected from the group consisting of a first high temperature stream discharged from the second purification part and injected into the mixed alcohol tank, a second high temperature stream discharged from the preliminary purification part and injected into the first alcohol tank, a third high temperature stream discharged from the trans reaction part and injected into the second washing part, a fourth high temperature stream discharged from the preliminary purification part and injected into the first washing part, and a fifth high temperature stream discharged from the separation part and injected into at least one of the first alcohol tank and the reaction part, and one or more low temperature streams selected from the group consisting of a first low temperature stream discharged from the second washing part and injected into the second purification part, a second low temperature stream discharged from the second alcohol tank and injected into the trans reaction part, a third low temperature stream discharged from the first washing part and injected into the first purification part, and a fourth low temperature stream discharged from the mixed alcohol tank and injected into the separation part.

First, in the heat exchange system of the present invention, the high temperature stream which is a target for heat exchanging includes five different high temperature streams of first to fifth high temperature streams.

The first high temperature stream is a stream discharged from the second purification part and injected into the mixed alcohol tank, and a mixed alcohol removed through a process such as distillation in the second purification part can have a gas or liquid phase. The alcohol present in a gas has a large volume, is difficult to store directly in the mixed alcohol tank and is required to be liquefied, and for the safe storage of the liquid phase, the temperature is required to be reduced further.

The second high temperature stream is a stream discharged from the preliminary purification part and injected into the first alcohol tank, and like the case of the first high temperature stream, the first alcohol removed through a process such as distillation can have a gas or liquid phase and is required to be cooled.

The third high temperature stream is a stream discharged from the trans reaction part and injected into the second washing part. Since trans esterification reaction performed in the trans reaction part is performed at a relatively high temperature, the stream discharged therefrom and injected into the second washing part also has a high temperature. The stream is then cooled in a neutralization and washing processes in the second washing part, and if a cooling process is performed in advance, energy amount consumed in the second washing part can be reduced. Accordingly, the third high temperature stream is required to be cooled.

The fourth high temperature stream is a stream discharged from the preliminary purification part and injected into the first washing part. Like the second high temperature stream, the fourth high temperature stream is discharged from the preliminary purification part and has a high temperature, and is required to be cooled because cooling is performed in subsequent neutralization and washing processes like the third high temperature stream.

The fifth high temperature stream is a stream discharged from the separation part and injected into at least one of the first alcohol tank and the reaction part. The separation of the mixed alcohol in the separation part can be accompanied with heating, and accordingly, the stream to be separated in the separation part and injected into at least one of the first alcohol tank and the reaction part is a high temperature stream. Accordingly, the alcohol is required to be cooled to inject into the first alcohol tank and the reactor, and the fifth high temperature stream is required to be cooled.

The temperature of the first to fifth high temperature streams can be changed according to the operation conditions of a process, or specific selection of dicarboxylic acid, first alcohol and second alcohol, which are reaction raw materials, but can be included in a range of about 150 to 250° C.

In the heat exchange system of the present invention, the low temperature stream which is a target for heat exchanging includes four different low temperature streams of first to fourth low temperature streams.

The first low temperature stream is a stream discharged from the second washing part and injected into the second purification part. The stream undergone a washing process has a relatively low temperature and is required to be heated because a mixed alcohol in the stream is required to be heated for separation in a subsequent purification part.

The second low temperature stream is a stream discharged from the second alcohol tank and injected into the trans reaction part. Since the second alcohol stored in the second alcohol tank is present in a liquid phase, this stream has a relatively low temperature and is required to be heated because reaction raw materials are required to be heated for the reaction in a subsequent trans reaction part.

The third low temperature stream is a stream discharged from the first washing part and injected into the first purification part, and like the first low temperature stream, has a low temperature through the washing process and is required to be heated for separating the first alcohol in the stream afterward.

The fourth low temperature stream is a stream discharged from the mixed alcohol tank and injected into the separation part. Like the second low temperature stream, the mixed alcohol stored in the mixed alcohol tank is present in a liquid state, and this stream has a relatively low temperature and is required to be heated because heating is required for separating the first alcohol and the second alcohol in a subsequent separation part.

The temperature of the first to fourth low temperature streams can be changed according to the operation conditions of a process, or specific selection of dicarboxylic acid, first alcohol and second alcohol, which are reaction raw materials, but can be included in a range of about 20 to 130° C.

The heat exchange part included in the heat exchange system of the present invention is configured to exchange heat between one or more high temperature streams selected from the first to fifth high temperature streams and one or more low temperature streams selected from the first to fourth low temperature streams. The heat exchange part includes one heat exchanging apparatus, but can include multiple heat exchanging apparatuses. In terms of maximizing the energy efficiency of a whole process, multiple heat exchanging apparatuses are preferable. If the multiple heat exchanging apparatuses are provided, the heat exchange part means a heat exchanging system itself including all the multiple heat exchanging apparatuses, and the type, shape, etc. of each heat exchanging apparatus are not specifically limited only if the object of heat exchanging can be accomplished, and the position thereof is not additionally limited as long as the position allows smooth heat exchange of the high temperature streams and the low temperature streams, which are targets for heat exchanging.

More particularly, the heat exchange system of the present invention can be configured as shown in FIGS. 2 to 11. The heat exchange systems shown in FIGS. 2 to 11 illustrate embodiments of the heat exchange system of the present invention, respectively, and show only streams which are targets for heat exchanging in the preparation system of a diester-based composition of FIG. 1, and the indication of remaining streams is omitted. A heat exchanger performing heat exchanging is indicated by HX. FIGS. 2 to 11 of the present disclosure illustrate embodiments of the heat exchange system of the present invention, and it is obvious that the scope of the present invention is not limited to the scope of FIGS. 2 to 11.

In the heat exchange system shown in FIG. 2, the heat exchange part is composed for heat exchanging the first high temperature stream with the third low temperature stream, heat exchanging the second high temperature stream and the third high temperature stream with the first low temperature stream, heat exchanging the fourth high temperature stream with the second low temperature stream, and heat exchanging the fifth high temperature stream with the fourth low temperature stream.

In the heat exchange system shown in FIG. 3, the heat exchange part is composed for heat exchanging the first high temperature stream with the second low temperature stream, heat exchanging the second high temperature stream and the third high temperature stream with the first low temperature stream, heat exchanging the fourth high temperature stream with the third low temperature stream, and heat exchanging the fifth high temperature stream with the fourth low temperature stream.

In the heat exchange system shown in FIG. 4, the heat exchange part is composed for heat exchanging the first high temperature stream with the second low temperature stream, heat exchanging the second high temperature stream and the third high temperature stream with the first low temperature stream, heat exchanging the fourth high temperature stream with the fourth low temperature stream, and heat exchanging the fifth high temperature stream with the third low temperature stream.

In the heat exchange system shown in FIG. 5, the heat exchange part is composed for heat exchanging the first high temperature stream with the second low temperature stream and the fourth low temperature stream, heat exchanging the second high temperature stream and the third high temperature stream with the first low temperature stream, and heat exchanging the fourth high temperature stream with the third low temperature stream.

In the heat exchange system shown in FIG. 6, the heat exchange part is composed for heat exchanging the first high temperature stream with the second low temperature stream and the fourth low temperature stream, heat exchanging the second high temperature stream and the third high temperature stream with the first low temperature stream, and heat exchanging the fifth high temperature stream with the third low temperature stream.

In the heat exchange system shown in FIG. 7, the heat exchange part is composed for heat exchanging the first high temperature stream with the fourth low temperature stream, heat exchanging the second high temperature stream and the third high temperature stream with the first low temperature stream, heat exchanging the fourth high temperature stream with the third low temperature stream, and heat exchanging the fifth high temperature stream with the second low temperature stream.

In the heat exchange system shown in FIG. 8, the heat exchange part is composed for heat exchanging the first high temperature stream with the third low temperature stream and the fourth low temperature stream, heat exchanging the second high temperature stream and the third high temperature stream with the first low temperature stream, heat exchanging the fourth high temperature stream with the third low temperature stream, and heat exchanging the fifth high temperature stream with the second low temperature stream.

In the heat exchange system shown in FIG. 9, the heat exchange part is composed for heat exchanging the first high temperature stream with the fourth low temperature stream, heat exchanging the second high temperature stream and the third high temperature stream with the first low temperature stream, heat exchanging the fourth high temperature stream with the second low temperature stream, and heat exchanging the fifth high temperature stream with the third low temperature stream.

In the heat exchange system shown in FIG. 10, the heat exchange part is composed for heat exchanging the first high temperature stream and the second high temperature stream with the first low temperature stream, heat exchanging the third high temperature stream with the fourth low temperature stream, heat exchanging the fourth high temperature stream with the second low temperature stream, and heat exchanging the fifth high temperature stream with the third low temperature stream.

In the heat exchange system shown in FIG. 11, the heat exchange part is composed for heat exchanging the first high temperature stream and the second high temperature stream with the first low temperature stream, heat exchanging the third high temperature stream with the fourth low temperature stream, heat exchanging the fourth high temperature stream with the third low temperature stream, and heat exchanging the fifth high temperature stream with the second low temperature stream.

EXPLANATION OF SYMBOLS

11: first alcohol tank
12: second alcohol tank
101: first alcohol stream
102: second alcohol stream (second low temperature stream)
21: reaction part
211: first reaction product stream
22: trans reaction part
221: second reaction product stream (third high temperature stream)
3: preliminary purification part
301: purified product stream (fourth high temperature stream)
302: purified product stream
303: unreacted first alcohol stream (second high temperature stream)
41: first washing part
411: first neutralized product stream (third low temperature stream)
42: second washing part
421: second neutralized product stream (first low temperature stream)
51: first purification part
511: first diester-based composition stream
512: unreacted first alcohol stream
52: second purification part
521: second diester-based composition stream
522: unreacted mixed alcohol stream (first high temperature stream)
61: mixed alcohol tank
611: mixed alcohol stream (fourth low temperature stream)
62: separation part
621: first alcohol stream (fifth high temperature stream)
622: second alcohol stream

The invention claimed is:

1. A preparation system of a diester-based composition having a heat exchange system, the preparation system comprising:
a first alcohol tank that stores and injects a first alcohol;
a second alcohol tank that stores and injects a second alcohol;
a reaction part that performs esterification reaction of the first alcohol and a dicarboxylic acid to produce a first reaction product;
a preliminary purification part that removes an unreacted first alcohol from the first reaction product to produce a purified product;
a trans reaction part that performs trans esterification reaction of the purified product and the second alcohol to obtain a second reaction product;
a first washing part that neutralizes and washes the purified product to obtain a first neutralized product;
a second washing part that neutralizes and washes the second reaction product to obtain a second neutralized product;
a first purification part that removes an unreacted first alcohol from the first neutralized product and injects the removed unreacted first alcohol into the first alcohol tank to obtain a remaining first diester-based composition;
a second purification part that removes a mixed alcohol of an unreacted first alcohol and a second alcohol from the second neutralized product and injects the removed mixed alcohol into a mixed alcohol tank to obtain a remaining second diester-based composition;
a mixed alcohol tank that cools and stores the mixed alcohol; and
a separation part that separates the mixed alcohol into a first alcohol and a second alcohol and injects thereof into at least one among the first alcohol tank and the reaction part, and the second alcohol tank, respectively,
wherein the heat exchange system comprises a heat exchange part including one or more heat exchangers,
wherein the heat exchange part exchanges heat between:
one or more high temperature streams selected from the group consisting of a first high temperature stream discharged from the second purification part and injected into the mixed alcohol tank, a second high temperature stream discharged from the preliminary purification part and injected into the first alcohol tank, a third high temperature stream discharged from the trans reaction part and injected into the second washing part, a fourth high temperature stream discharged from the preliminary purification part and injected into the first washing part, and a fifth high temperature stream discharged from the separation part and injected into the first alcohol tank, and one or more low temperature streams selected from the group consisting of a first low temperature stream discharged from the second washing part and injected into the second purification part, a second low temperature stream discharged from the second alcohol tank and injected into the trans reaction part, a third low temperature stream discharged from the first washing part and injected into the first purification part, and a fourth low temperature stream discharged from the mixed alcohol tank and injected into the separation part.

2. The preparation system of a diester-based composition according to claim 1, wherein the heat exchange part exchanges heat between the selected one high temperature stream and the selected multiple low temperature streams.

3. The preparation system of a diester-based composition according to claim 1, wherein the heat exchange part exchanges heat between the selected multiple high temperature streams and the selected one low temperature stream.

4. The preparation system of a diester-based composition according to claim 1, wherein the heat exchange part exchanges heat between:
the first high temperature stream and the third low temperature stream,
the second and third high temperature streams and the first low temperature stream,
the fourth high temperature stream and the second low temperature stream, and
the fifth high temperature stream and the fourth low temperature stream.

5. The preparation system of a diester-based composition according to claim 1, wherein the heat exchange part exchanges heat between:
the first high temperature stream and the second low temperature stream,
the second and third high temperature streams and the first low temperature stream,
the fourth high temperature stream and the third low temperature stream, and
the fifth high temperature stream and the fourth low temperature stream.

6. The preparation system of a diester-based composition according to claim 1, wherein the heat exchange part exchanges heat between:
the first high temperature stream and the second low temperature stream,
the second and third high temperature streams and the first low temperature stream,
the fourth high temperature stream and the fourth low temperature stream, and
the fifth high temperature stream and the third low temperature stream.

7. The preparation system of a diester-based composition according to claim 1, wherein the heat exchange part exchanges heat between:
the first high temperature stream and the second and fourth low temperature streams,
the second and third high temperature streams and the first low temperature stream, and
the fourth high temperature stream and the third low temperature stream.

8. The preparation system of a diester-based composition according to claim 1, wherein the heat exchange part exchanges heat between:
the first high temperature stream and the second and fourth low temperature streams,
the second and third high temperature streams and the first low temperature stream, and
the fifth high temperature stream and the third low temperature stream.

9. The preparation system of a diester-based composition according to claim 1, wherein the heat exchange part exchanges heat between:
the first high temperature stream and the fourth low temperature stream,
the second and third high temperature streams and the first low temperature stream,
the fourth high temperature stream and the third low temperature stream, and
the fifth high temperature stream and the second low temperature stream.

10. The preparation system of a diester-based composition according to claim 1, wherein the heat exchange part exchanges heat between:
the first high temperature stream and the third and fourth low temperature streams,
the second and third high temperature streams and the first low temperature stream,
the fourth high temperature stream and the third low temperature stream, and
the fifth high temperature stream and the second low temperature stream.

11. The preparation system of a diester-based composition according to claim 1, wherein the heat exchange part exchanges heat between:
the first high temperature stream and the fourth low temperature stream,
the second and third high temperature streams and the first low temperature stream,
the fourth high temperature stream and the second low temperature stream, and
the fifth high temperature stream and the third low temperature stream.

12. The preparation system of a diester-based composition according to claim 1, wherein the heat exchange part exchanges heat between:
the first and second high temperature streams and the first low temperature stream,
the third high temperature stream and the fourth low temperature stream,
the fourth high temperature stream and the second low temperature stream, and
the fifth high temperature stream and the third low temperature stream.

13. The preparation system of a diester-based composition according to claim 1, wherein the heat exchange part exchanges heat between:
the first and second high temperature streams and the first low temperature stream,
the third high temperature stream and the fourth low temperature stream,
the fourth high temperature stream and the third low temperature stream, and
the fifth high temperature stream and the second low temperature stream.

* * * * *